United States Patent [19]

Okabe et al.

[11] Patent Number: 5,977,414
[45] Date of Patent: Nov. 2, 1999

[54] 2,3-DIHALOGENO-6-TRIFLUOROMETHYLBENZENE DERIVATIVES AND PROCESSES FOR THE PREPARATION THEREOF

[75] Inventors: Takashi Okabe; Isamu Kasahara; Tatsumi Suzuki, all of Kanagawa, Japan

[73] Assignee: Nippon Soda Co., Ltd., Tokyo, Japan

[21] Appl. No.: 09/043,894

[22] PCT Filed: Jul. 29, 1997

[86] PCT No.: PCT/JP97/02613

§ 371 Date: Mar. 30, 1998

§ 102(e) Date: Mar. 30, 1998

[87] PCT Pub. No.: WO98/04509

PCT Pub. Date: Feb. 5, 1998

[30] Foreign Application Priority Data

| | | | |
|---|---|---|---|
| Jul. 30, 1996 | [JP] | Japan | 8-216688 |
| Aug. 9, 1996 | [JP] | Japan | 8-227559 |
| Apr. 4, 1997 | [JP] | Japan | 9-086328 |

[51] Int. Cl.$^6$ ................................................. C07C 45/42
[52] U.S. Cl. .......................... 568/437; 568/425; 568/426; 568/435
[58] Field of Search ..................... 568/425, 435, 568/426, 437, 438; 564/259, 265, 237

[56] References Cited

U.S. PATENT DOCUMENTS

| | | | |
|---|---|---|---|
| 4,268,525 | 5/1981 | Paul | 424/326 |
| 4,939,140 | 7/1990 | Larson | 514/222 |
| 5,041,683 | 8/1991 | Marhold et al. | 568/425 |

FOREIGN PATENT DOCUMENTS

| | | |
|---|---|---|
| WO96/19442 | 6/1996 | WIPO . |
| WO97/00845 | 1/1997 | WIPO . |

OTHER PUBLICATIONS

Paquette, Encyclopedia of Reagents for Organic Synthesis, vol. 5, pp. 3504–3505, 1995.

Bridges et al, Tetrahedron Letters, vol. 33, No. 49, 1992, pp. 7499–7502.

Primary Examiner—Shailendra Kumar
Assistant Examiner—Sreeni Padmanabhan
Attorney, Agent, or Firm—Jacobson, Price, Holman & Stern, PLLC

[57] ABSTRACT

2,3-Dihalogeno-6-trifluoromethylbenzaldehydes of general formula (I) useful as intermediates for the preparation of fungicides for agricultural and horticultural use;a process for the preparation of the same; and process for preparing 2,3-dihalogeno-6-trifluoromethylbenzamidoximes of general formula (IV) from the above compounds, wherein $X^1$ and $X^2$ are each independently fluoro, chloro or bromo.

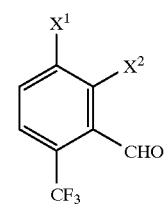

(1)

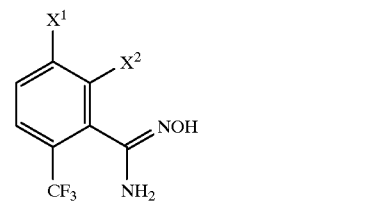

(IV)

3 Claims, No Drawings

2,3-DIHALOGENO-6-TRIFLUOROMETHYLBENZENE DERIVATIVES AND PROCESSES FOR THE PREPARATION THEREOF this is the U.S. National Stage Application of PCT/JP97/02,613 filed Jul. 29, 1997 now WO98/04509 published Feb. 5, 1998.

FIELD OF THE INVENTION

The present invention is related to 2,3-dihalogeno-6-trifluoromethylbenzaldehyde useful as intermediates for producing agrohorticultural bactericides, a process for producing the said compounds, and a process for producing 2,3-dihalogeno-6-trifluoromethylbenzamidoxime from the said compounds.

BACKGROUND ART

Known conventional methods to introduce a formyl group into an aromatic ring are to react alkyl lithium, such as n-butyl lithium, with N,N-dimethylformamide (DMF) or N-phenyl-N-methylformamide, to react alkyl lithium with formate, such as methyl formate, and the like.

For example, European Patent Laid-open specifications Nos. 125803 and 174131 describe a method to react 2,5-difluorobenzotrifluoride with n-butyl lithium and N-phenyl-N-methylformamide. However, this formylation reaction usually gives two reaction products, not being selective.

In the case of the reaction of 3,4-dichlorobenzotrifluoride with n-butyl lithium and DMF, 2,3-dichloro-5-trifluoromethylbenzaldehyde is the main product, as described later.

In the Japanese Patent Laid-open No. Hei 3-5436 Gazette, compounds represented by the general formula (Ia), which contain the compounds of this invention, are described.

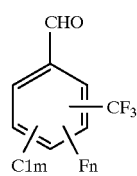

(Ia)

Conventionally 2,3-dihalogeno-6-trifluoromethylbenzamidoximes have been produced via 2,3-dihalogeno-6-trifluoromethylbenzonitrile (refer to WO/19442 Gazette). However, this method had problems of low yield and long reaction processes.

DISCLOSURE OF THE INVENTION

The present invention is directed to 2,3-dihalogeno-6-trifluoromethylbenzaldehydes, an outstanding industrial process for producing the same, and an excellent industrial process for producing 2,3-dihalogeno-6-trifluoromethylbenzamidoxime by using 2,3-halogeno-6-trifluoromethylbenzaldehyde as a starting material.

The present invention is directed to (1) the compounds represented by a general formula (I)

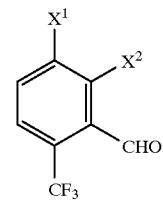

(I)

wherein $X^1$ and $X^2$ are the same or different and each independently a fluorine, chlorine or bromine atom, (2) a process for producing the compounds represented by the general formula (I)

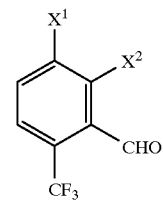

(I)

wherein $X^1$ and $X^2$ are as defined above, characterized in that the compound is obtained by reacting a compound represented by a general formula (II)

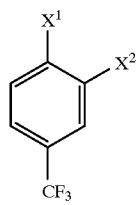

(II)

wherein $X^1$ and $X^2$ are as defined above, with n-butyl lithium and formate and (3) a process for producing 2,3-dihalogeno-6-trifluoromethylbenzamidoxime represented by a general formula (IV)

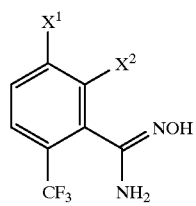

(IV)

wherein $X^1$ and $X^2$ are as defined above, characterized in that the compound is obtained by oximating a compound represented by the above general formula (I) to produce a compound represented by a general formula (III)

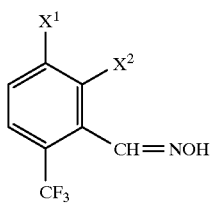

(III)

wherein $X^1$ and $X^2$ are as defined above, then subsequently by amide oximating the said compound.

The process (2) of this invention is described below:

A 3,4-dihalogenobenzotrifluoride is reacted with an alkylated lithium, such as n-butyl lithium and formate, in solvents, while cooling at the temperature of −30∼−70° C.

Solvents to be used in the reaction are not particularly restricted if they are inert, for example, ethers such as tetrahydrofuran (THF), dioxane and diethyl ether, aromatic hydrocarbons such as toluene and xylene, and saturated hydrocarbons such as hexane and pentane. These solvents can be used alone or a mixture thereof.

The examples of formates used for the reaction are methyl formate, ethyl formate, propyl formate, isopropyl formate, butyl formate, t-butyl formate, phenyl formate and benzyl formate. The use of methyl formate and ethyl formate is particularly preferable due to easy handling and production cost.

As the 2,3-dihalogeno-6-trifluoromethylbenzaldehyde compounds of this invention, the following can be given:
1: 2,3-dichloro-6-trifluoromethylbenzaldehyde $^1$H-NMR (CDCl$_3$, δppm from TMS): 7.64 (1H, d, J=8.5 Hz), 7.74 (1H, d, J=8.5 Hz), 10.44 (1H, s)
2: 2,3-difluoro-6-trifluoromethylbenzaldehyde $^1$H-NMR (CDCl$_3$, δppm from TMS): 7.49 (1H, q, J=9.0 Hz), 7.61 (1H, dd, J=9.0 Hz, J=4.8 Hz), 10.39 (1H, s)
3: 2,3-dibromo-6-trifluoromethylbenzaldehyde
4: 2-chloro-3-fluoro-6-trifluoromethylbenzaldehyde $^1$H-NMR (CDCl$_3$, δppm from TMS) 7.42 (1H, t, J=8.7 Hz), 7.72 (1H, dd, J=8.7 Hz, J=4.8 Hz), 10.45 (1H, s)
5: 3-chloro-2-fluoro-6-trifluoromethylbenzaldehyde $^1$H-NMR (CDCl, δppm from TMS) 7.74 (1H, t, J=8.0 Hz), 7.57 (1H, d, J=8.0 Hz), 10.40 (1H, s)
6: 2-bromo-3-chloro-6-trifluoromethylbenzaldehyde
7: 2-bromo-3-fluoro-6-trifluoromethylbenzaldehyde
8: 3-bromo-2-chloro-6-trifluoromethylbenzaldehyde
9: 3-bromo-2-fluoro-6-trifluoromethylbenzaldehyde The process (3) of this invention for producing 2,3-halogeno-6-trifluoromethylbenzamide oximes from the above-mentioned benzaldehydes is described below: The first process of this invention, the oximating reaction from a compound represented by the general formula (I) to a compound represented by the general formula (III), is a reaction with hydroxylamine in inert solvents. The hydroxylamine can be in the form of hydrochloride or sulfate. There are no particular restrictions on solvents used for the reaction if they are inert. Examples are alcohols such as methanol, ethanol, propanol and isopropanol, water and acetonitrile. The reaction proceeds smoothly within the temperature range from room temperature to the boiling point of the solvent used.

The second process, the amide oximating reaction from a compound represented by the general formula (III) to a compound represented by the general formula (IV), is a reaction with a halogenating agent in inert solvents to produce imidoyl halide (V) followed by a reaction with ammonia.

There are no particular restrictions on solvents used for the reaction if they are inert. For example, in the halogenation process, halogenated hydrocarbons, such as dichloromethane, chloroform, carbon tetrachloride and 1,2-dichloroethane, can be used. In the process of amide oximation, examples are alcohols such as methanol, ethanol, propanol and isopropanol, water and acetonitrile.

Examples of halogenating agents include N-chlorosuccinimide, N-bromosuccinimide, chlorine, bromine, surfuryl chloride and hypochlorite. Ammonia can be used in the form of ammonia gas and an alcohol solution, such as methanol and ethanol, of ammonia, and as well as aqueous ammonia. The reaction proceeds smoothly within the temperature range from −10° C. to the boiling point of the solvent used.

The production process of the present invention is described below:

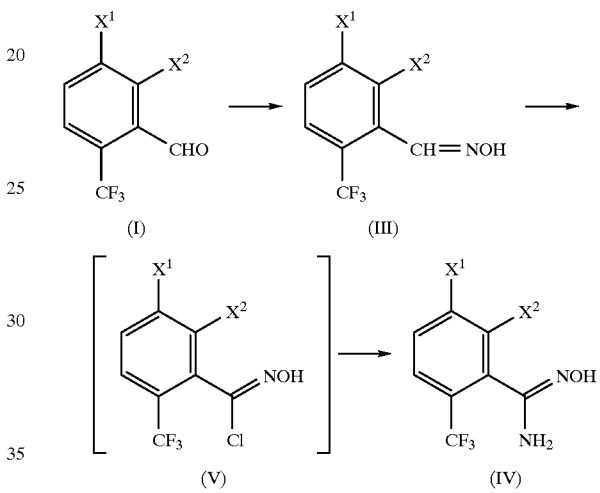

Compounds represented by the general formula (III) can be derived to benzonitrile represented by a general formula (VI)

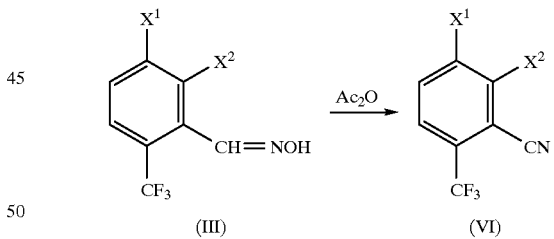

wherein $X^1$ and $X^2$ are as defined above, by reacting with acetic anhydride. The reaction is usually carried out by heating a compound represented by the general formula (III) in acetic anhydride under reflux. The compound is also useful as an intermediate for agrochemicals.

In each case, the objective compounds can be obtained by usual post-treatment after the reaction is completed. The structure of the compounds of this invention was decided from IR, NMR, MASS and other available means.

BEST MODE FOR CARRYING OUT THE INVENTION

The present invention is further described in detail with reference to the following examples. This invention is not restricted by the examples.

EXAMPLE 1

Synthesis of 2,3-dichloro-6-trifluoromethylbenzaldehyde

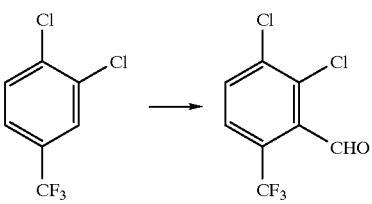

54 g (0.25 mol) of 3,4-dichlorobenzotrifluoride was dissolved in 500 ml of anhydrous THF, and cooled down to −70° C. with dry ice/acetone. To the solution, 190 ml (0.3 mol) of hexane solution of n-butyl lithium was added dropwise over 45 minutes, while keeping the temperature at −70 ° C. The reaction solution was matured for an hour at −70° C., then 30 g (0.5 mol) of methyl formate was dropped into the solution over 30 minutes, while keeping the temperature at −70 ° C. After the reaction solution was matured for an hour at −70 ° C., the temperature of the solution was elevated to room temperature. The reaction solution was poured into ice water and extracted with ether. The organic layer obtained was washed with water and then dried over anhydrous magnesium sulfate. The solvent was distilled out under reduced pressure. The resulting residue was distilled to give 47.3 g of oily product. Yield 77% (purity 95%), 84~94° C./3mmHg.

EXAMPLE 2

Example 1 was repeated except carrying out the reaction at −45° C. Yield (weight) 42.0 g, (yield 68.9%, purity 93%).

EXAMPLE 3

Synthesis of 2,3-difluoro-6-trifluoromethylbenzaldehyde

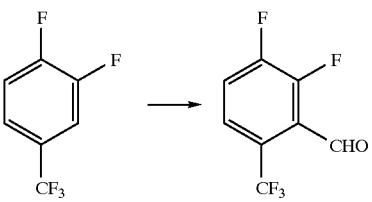

2.73 g (0.015 mol) of 3,4-difluorobenzotrifluoride was dissolved in 27 ml of anhydrous THF, and cooled down to −70° C. with dry ice/acetone. To the solution, 9.4 ml (0.015 mol) of 1.6M hexane solution of n-butyl lithium was slowly added dropwise, while keeping the temperature from −70° C. to −45 ° C. The reaction solution was matured for 2 hours at −45° C. Subsequently 1.8 g (0.03 mol) of methyl formate was added to the solution dropwise over 30 minutes, while keeping the temperature at −45° C. After the reaction solution was matured for an hour at −45° C., the temperature of the solution was elevated to room temperature. The reaction solution was poured into ice water and extracted with ether. The organic layer obtained was washed with water and then dried over anhydrous magnesium sulfate. The solvent was distilled out under reduced pressure. The resulting residue was purified through silica gel column chromatography to give 2.7 g of the title compound. Yield 85%, nD (20) 1.4357.

2,3-Dichloro-6-trifluoromethylbenzaldehyde obtained in Examples 1 and 2, when used as a starting material, can be derived to 2-fluoro-3-chloro-6-trifluoromethylbenzaldehyde and 2,3-difluoro-6-trifluoromethylbenzaldehyde according to the methods described in Houben-Weyl, Methoden der Org. Chemie, Volume E3, page 350. The reaction is usually carried out using a fluoride, such as sodium fluoride, potassium fluoride and cesium fluoride, in an inert solvent, such as sulfolane, dimethylsulfoxide and DMF, in the presence of a catalyst, if required, including crown ether, a phosphonium salt, such as tetraphenylphosphonium bromide and tetrabutylphosphonium bromide, and an ammonium salt, such as tetramethylammonium chloride, tetraethylammonium chloride, tetrabutylammonium iodide and benzyl tributylammonium chloride, within the temperature range from room temperature to the reflux temperature of the

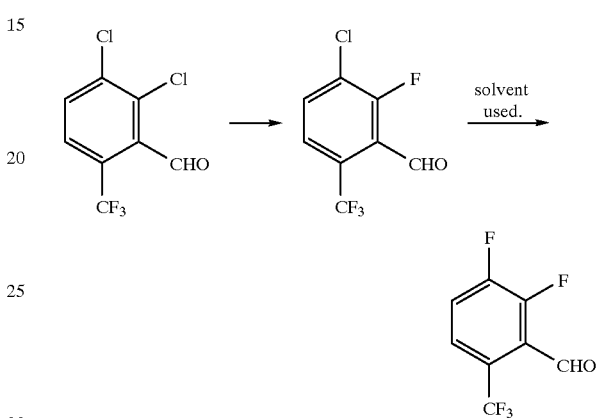

COMPARATIVE EXAMPLE 1

Synthesis of 2,3-dichloro-5-trifluoromethylbenzaldehyde

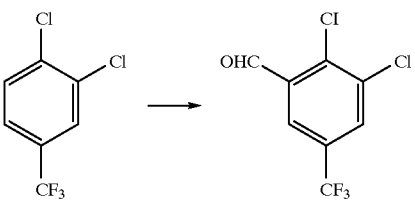

57.3 g of 3,4-dichlorobenzotrifluoride was dissolved in 500 ml of dried tetrahydrofuran under nitrogen atmosphere and was cooled down to −78° C. To the resulting solution was dropped 200 ml of 1.6M hexane solution of n-butyl lithium. After the solution was further stirred for about 1.5 hours at the same temperature, 38.9 g of DMF was added dropwise into the reaction solution. After the completion of the addition, the temperature of the reaction system was gradually elevated to room temperature, while checking the progress of the reaction. Ice water was added to the reaction solution to extract with ether. The extract was dried over anhydrous magnesium sulfate. The solvent was distilled under reduced pressure. The obtained oily product was distilled under reduced pressure to give 45.3 g of oily residue (bp. 70~85° C./2 mmHg). The analysis of the purity of the obtained residue by gas chromatography revealed that it was a mixture of 2,3-dichloro-5-trifluoromethylbenzaldehyde and 2,3-dichloro-6-trifluoromethylbenzaldehyde at the ratio of 7:1.

The NMR data of 2,3-dichloro-5-trifluoromethylbenzaldehyde is as follows:

$^1$H-NMR (CDCl$_3$, δppm from TMS): 7.97 (1H, d), 8.11 (1H, d), 10.50 (1H, s)

EXAMPLE 4

(Synthesis of 2,3-dichloro-6-trifluoromethylbenzaldehyde oxime)

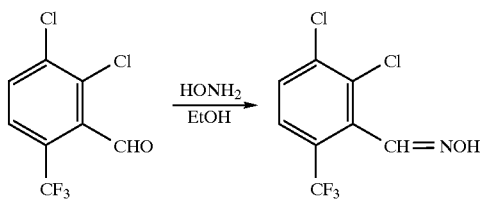

4.86 g (0.02 mol) of 2,3-dichloro-6-trifluoromethylbenzaldehyde was dissolved in 30 ml of ethanol. To the solution 2.78 g (0.04 mol) of hydroxylamine hydrochloride was added to heat under reflux for an hour. The reaction solution was cooled down and poured into ice water. The resulting solution was extracted with ethyl acetate. The organic layer was washed with water and dried over anhydrous magnesium sulfate. The solvent was distilled under reduced pressure to give 5.0 g of the title compound. Yield 97%, mp. 102~104° C.

EXAMPLE 5

(Synthesis of 2,3-difluoro-6-trifluoromethylbenzaldehyde oxime)

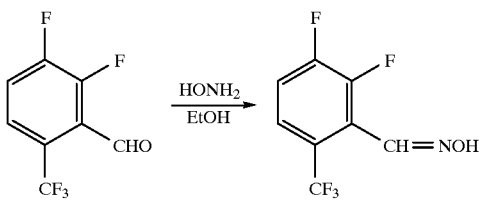

9.0 g (42.8 mmol) of 2,3-difluoro-6-trifluoromethylbenzaldehyde was dissolved in 50 ml of ethanol. 3.39 g (85.6 mmol) of hydroxylamine hydrochloride was added to the resulting solution to heat under reflux for an hour. The reaction solution was cooled down, and poured into ice water. The solution was extracted with ethyl acetate. The organic layer was washed with water and dried over anhydrous magnesium sulfate. The solvent was distilled under reduced pressure to give 9.4 g of the title compound. Yield 97.6%, mp. 111~112° C.

EXAMPLE 6

(Synthesis of 2,3-difluoro-6-trifluoromethylbenzamidoxime)

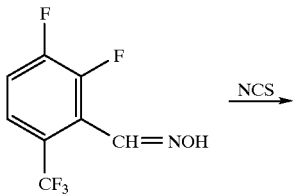

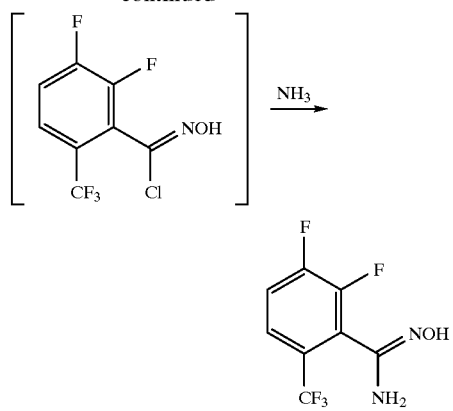

2.25 g (10 mmol) of 2,3-difluoro-6-trifluoromethylbenzaldehyde oxime was dissolved in 20 ml of chloroform. While cooling with ice water, 1.59 g (12 mmol) of N-chlorosuccinimide was added to the solution. After the temperature of the solution was elevated to room temperature, the solution was stirred for 2 hours. Compounds with low boiling point were distilled under reduced pressure, then ether was added to the residue. The precipitated crystals were separated by filtration. The filtrate was added dropwise into 10 ml of ethanol solution containing 0.5 g (30 mmol) of ammonia and stirred for 30 minutes. The solvent was distilled under reduced pressure. The residue was extracted with ethyl acetate. The organic layer was washed with water and dried over anhydrous magnesium sulfate. The solvent was distilled under reduced pressure to give 1.9 g of the title compound. Yield 79.2%, mp 105~107° C.

EXAMPLE 7

(Synthesis of 2,3-difluoro-6-trifluoromethylbenzamidoxime)

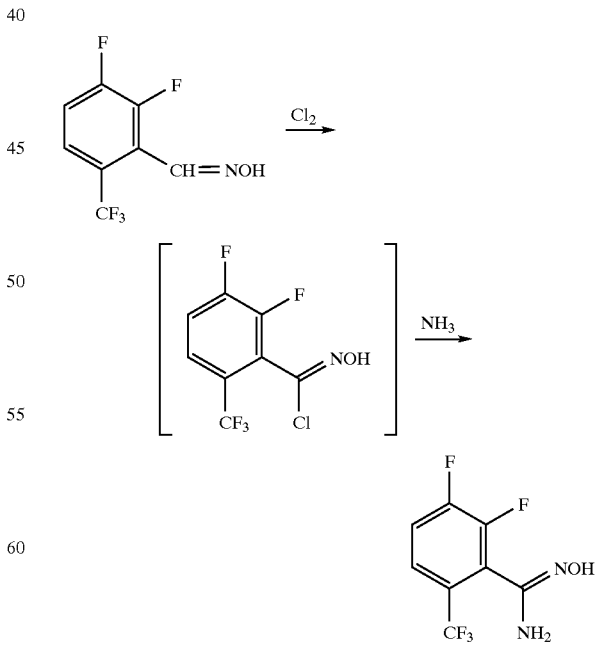

3.5 g (15 mmol) of 2,3-difluoro-6-trifluoromethylbenzaldehyde oxime was dissolved in 20 ml of chloroform. 2 g (30 mmol) of chlorine gas was blown into the resulting solution over 30 minutes, while cooling with ice water. The temperature of the reaction solution was elevated to room temperature and the solution was stirred further for 2 hours. Compounds with low boiling point were distilled from the reaction solution under reduced pressure. The resulting residue was dropped into a mixed solution of 4.6 g of 28% aqueous ammonia and 20 ml of ethanol, and stirred for 30 minutes. The reaction solution was concentrated under reduced pressure. The obtained residue was extracted with ethyl acetate. The organic layer was washed with water and dried over anhydrous magnesium sulfate. The solvent was distilled under reduced pressure to give 2.72 g of the title compound. Yield 72.9%.

REFERENCE EXAMPLE 1

(Synthesis of 2,3-dichloro-6-trifluoromethylbenzonitrile)

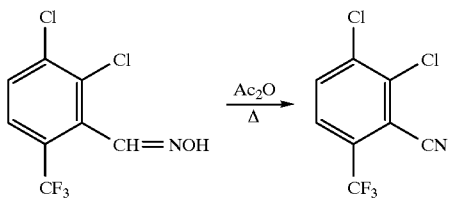

5.0 g (19.3 mmol) of 2,3-dichloro-6-trifluoromethylbenzaldehyde oxime was dissolved in 20 ml of acetic anhydride. The resulting solution was heated under reflux for 4 hours. Excessive acetic anhydride was distilled from the reaction solution under reduced pressure. The residue was dissolved with ethyl acetate. The obtained solution was washed with water and dried over anhydrous magnesium sulfate. The solvent was distilled under reduced pressure. The obtained product was purified by distillation to give 4.2 g of the title compound. Yield 90.3%, mp 53~54° C.

REFERENCE EXAMPLE 2

(Synthesis of 2,3-difluoro-6-trifluoromethylbenzonitrile)

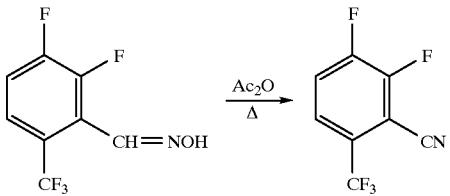

3.0 g (13.3 mmol) of 2,3-difluoro-6-trifluoromethylbenzaldehyde oxime was dissolved in 12 ml of acetic anhydride. The resulting solution was heated under reflux for 4 hours. Excessive acetic anhydride was distilled from the reaction solution under reduced pressure. The residue was dissolved with ethyl acetate. The obtained solution was washed with water and dried over anhydrous magnesium sulfate. The solvent was distilled under reduced pressure. The obtained product was purified by distillation to give 2.33 g of the title compound. Yield 84.4%, mp 98~100° C./25 mmHg.

Industrial Use

As described in the above, the present invention is related to novel 2,3-dihalogeno-6-trifluoromethylbenzene derivatives. The compounds of this invention are useful as intermediates for agrochemicals, pharmaceuticals, and particularly agrohorticultural bacteriocides. With the use of the methods of this invention, 2,3-dihalogeno-6-trifluoromethylbenzaldehyde compounds and 2,3-dihalogeno-6-trifluoromethylbenzamide oximes can be produced simply and highly selectively with high yield.

What is claimed is:

1. A process for producing 2,3-dihalogeno-6-trifluoromethylbenzaldehyde represented by a formula (I)

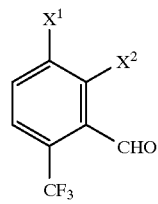

wherein $X^1$ and $X^2$ are the same or different and each independently represent a fluorine, chlorine or bromine atom, comprising reacting a compound represented by a formula (II)

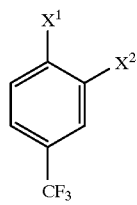

wherein $X^1$ and $X^2$ are as defined above with alkyl lithium and formate.

2. The process of claim 1 wherein the alkyl lithium is n-butyl lithium.

3. The process of claim 1 wherein the formate is methyl formate or ethyl formate.

* * * * *